United States Patent
Heymann et al.

(10) Patent No.: US 6,932,237 B2
(45) Date of Patent: Aug. 23, 2005

(54) METHOD AND DEVICE FOR GENERATING A MULTI-COMPONENT COMPOUND

(75) Inventors: Rudolf Heymann, Geesthacht (DE); Frauke Röbel, Hamburg (DE); Hans Hörth, Hamburg (DE)

(73) Assignee: Ernst Muhlbauer GmbH & Co. KG, Norderfriedrichskoog (DE)

( * ) Notice: Subject to any disclaimer, the term of this patent is extended or adjusted under 35 U.S.C. 154(b) by 447 days.

(21) Appl. No.: 10/200,356

(22) Filed: Jul. 22, 2002

(65) Prior Publication Data

US 2003/0022128 A1 Jan. 30, 2003

(30) Foreign Application Priority Data

Jul. 26, 2001 (EP) ............................................ 01118143

(51) Int. Cl.⁷ ................................................. B67B 7/00
(52) U.S. Cl. .............................. 222/1; 222/63; 222/94; 222/137; 222/145.6; 222/325; 222/326
(58) Field of Search .............................. 222/1, 58, 63, 222/94, 135–137, 145.1, 52, 145.5–145.6, 325–327, 333, 95, 105, 386

(56) References Cited

U.S. PATENT DOCUMENTS

| | | | |
|---|---|---|---|
| 4,341,327 A | | 7/1982 | Zeitz |
| 4,493,286 A | | 1/1985 | Carson |
| 4,854,482 A | * | 8/1989 | Bergner ........................ 222/94 |
| 5,020,693 A | * | 6/1991 | Ernst et al. ................... 222/137 |
| 5,370,273 A | * | 12/1994 | Rohloff et al. ............... 222/132 |
| 5,605,252 A | * | 2/1997 | Owen et al. .................... 222/1 |
| 5,816,445 A | * | 10/1998 | Gardos et al. .................. 222/1 |
| 6,047,861 A | * | 4/2000 | Vidal et al. ................... 222/137 |
| 6,126,039 A | | 10/2000 | Cline et al. |
| 6,315,164 B1 | * | 11/2001 | Muhlbauer et al. ............ 222/63 |
| 6,631,829 B1 | * | 10/2003 | Wagner et al. ................. 222/23 |

FOREIGN PATENT DOCUMENTS

| | | |
|---|---|---|
| DE | 199 51 504 A1 | 5/2001 |
| EP | 1 010 401 A1 | 6/2000 |
| WO | WO 00/38841 * 7/2000 | ......... B05C/17/005 |

* cited by examiner

Primary Examiner—Frederick Nicolas
(74) Attorney, Agent, or Firm—Alix, Yale & Ristas, LLP (57) ABSTRACT

The device for generating a multi-component compound, in particular for dental purposes, by pressing out and mixing its components from cartridges (5), which open into a mixer (10), is characterized in that the advance speed of the motor (15) is regulated by the pressing-out behaviour of the components, which pressing-out behaviour can be determined by sensors (III–VIII).

21 Claims, 7 Drawing Sheets

METHOD AND DEVICE FOR GENERATING A MULTI-COMPONENT COMPOUND

BACKGROUND OF THE INVENTION

The invention relates to a method and a device for generating a multi-component compound, in particular for dental purposes, by pressing its components out from exchangeable cartridges, which are arranged alongside one another and open into a mixer, by jointly advancing their plungers by means of an electric drive, in which the advance speed is regulated.

In a known method and a known device of this type (EP 1 010 401 A1), the plungers are at first advanced rapidly. When contact with the components then takes place, the resistance increases, and this is detected. The advance speed is then regulated to a lower constant value in order to ensure that the components are pressed out at a uniform speed. However, it has now been found that in many cases it is not sufficient to regulate the advance speed to a constant value, and instead it is also necessary to select the suitable advance speed. The dentist can of course do this by using already known apparatus. However, in most cases he will not succeed in setting the optimum advance speed. Different types of material have very different viscosities or require particular speeds due to processing factors. A universal adaptation does not take sufficient account of the large number of types of material. Depending on the properties of the material, there is an optimum advance and a good and reproducible result of the work. This is all the more so when the mixer used for the two combined components is not a static mixer, but a dynamic mixer driven by an electric motor. The speed too of this electric motor must then be adapted to the special requirements of the components so that the multi-component compound has the optimum properties.

If the advance and/or the speed of the mixer motor is not set optimally, the following problems can arise.

1. An unsuitable ratio of the speeds of advance and mixer shaft results in a non-optimum mixing of the components. Thus, conditions such as processing times and strengths of the impression are only partly achieved or not adequately achieved.
2. Depending on the viscosity of the material type, a wrong speed of the mixer shaft can result in inadmissibly high shearing, which means that the setting behaviour of the compounds is allowed to increase in an uncontrolled manner.
3. If the components have different flow behaviour, incorrect quantities are dispensed by a rigid speed of rotation. These lead to partial hardening or delays in the impression-taking. This can be compensated for or considerably improved by start and stop ramps.
4. If compounds are dispensed too quickly, a deformation of the pressure vessels or cartridges must be expected. The deformation leads to a change in the volume and thus to an inaccurate dosing of the components. This is all the more problematic if, for example, a container deforms more strongly than the second component. The error can impair the mechanical values of the impression and lead to partial hardening.
5. If compounds are used which have to be placed with precision and accurate dosing, an ideal dispensing speed is helpful. By this means, air inclusions and excess dosing are avoided.

SUMMARY OF THE INVENTION

The object of the invention is to make available a method and a device with which the advance speed is automatically regulated to a suitable value for the corresponding material. The solution according to the invention lies in the fact that the regulation of the advance speed is effected as a function of the pressing-out behaviour of the components, which behaviour is compared with stored or calculated values for known materials.

The pressing-out behaviour is thus measured. If, for example, there is only a relatively low resistance to pressing-out, then the components involved are evidently of low viscosity, which already permits conclusions to be drawn concerning the material used if the measured pressing-out pressure or the force is compared with stored values of various materials. After the material has thus been identified, the advance speed can be set to the optimum value for this material. The force or pressure needed for the pressing-out can be measured via the current consumption or the torque of the electric drive for the advance.

In an advantageous embodiment, the pressing-out pressure of one or all of the components is measured. Instead of the pressure, the pressing-out force can of course also be measured if the cross section of the plungers is known. This pressing-out force is very much dependent on the material. The pressing-out force in a particular apparatus is, for example, 283 N for Honigum as the base component and 1124 N as the catalyst component. In the case of the material Silagum, these forces are 1014 N as the base component and 1234 N as the catalyst component. If these forces are measured and compared with the stored values for these materials, it is possible to ascertain automatically which material is to be processed, so that the advance speed and if appropriate also the mixing speed can be optimally set accordingly.

If the advance speed is measured together with the current consumption or the torque of the electric drive for the advance, values for the flowability of the materials can be determined from this and can likewise be compared with known stored values and used for the regulating.

Moreover, the deformation of one or all of the cartridges or the deformation of the cartridge holder can be measured, which likewise permits conclusions to be drawn regarding the flow behaviour and can thus be used for identifying the material used and for optimum regulation.

If a mixer driven by an electric motor is provided, the current consumption or the torque of the electric motor can be measured, which likewise permits conclusions to be drawn regarding the viscosity of the material and thus, by comparison with stored values, regarding which material is involved. The speed of rotation for the electric motor of the mixer can then likewise be regulated to a suitable value.

The viscosity or flowability of the materials often critically depends on the temperature. Provision is therefore advantageously made for the temperature also to be measured, specifically either the temperature of the components before mixing or the temperature in the mixer. By measuring the pressing-out behaviour and comparing it with known pressing-out data, the material being used can therefore be identified and the pressing-out speed and if appropriate the speed of rotation of the mixer motor can be optimally set. By means of the method according to the invention and the device according to the invention, transitions from one behaviour to another can also be determined, compared and used for regulation, for example the thixotropy characteristic. The measurements can in this case be used not only for regulation, but can also serve to avoid overloads. In addition, provision can also be made for the dentist to be able to set a speed which he considers to be the optimum speed. If this does not correspond to the optimum advance speed which was determined by the apparatus, either a warning can be displayed or a "compromise" can be reached between the set speed and the automatically determined speed.

The speed of rotation for the advance motor and if appropriate for the mixer motor is regulated according to known techniques. Direct-current motors are preferably used which have a voltage range of 12 to 24 volts and whose speed is dependent on the voltage. The speed of the motors can also be influenced by a pulse-width modulation, in which case the torque remains substantially constant. The invention is described below on the basis of advantageous embodiments and with reference to the attached drawings, in which:

BRIEF DESCRIPTION OF THE DRAWINGS

The invention is described below on the basis of advantageous embodiments and with reference to the attached drawings, in which.

DETAILED DESCRIPTION OF THE PREFERRED EMBODIMENT

Figure 1:
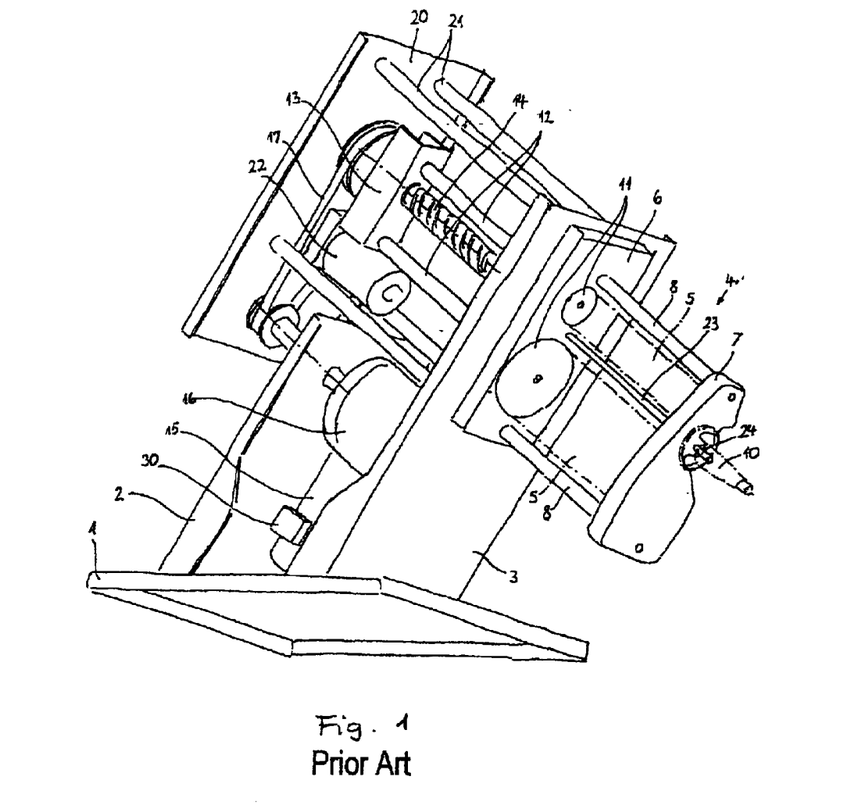
FIG. 1 shows a previously known apparatus in the opened state, in a perspective view.

A known apparatus (EP 1 010 401 A1) in which the invention can be applied will first be described with reference to FIG. 1.

Rising from a base part 1, there are support plates 2, 3. A holder 4 is provided on the latter for cartridges 5, indicated by dot-and-dash lines. In this context it is of no importance whether the cartridges, which are preferably of cylindrical design, are filled directly with the components or receive an optionally exchangeable tubular bag containing the component.

The holder 4 comprises a rear holding plate 6 and a front holding plate 7 which are held together by anchors 8. The cartridges 5 can be fitted between these. Further holding means (not shown) can be provided to act on the lateral positioning of the cartridges 5.

On the front holding plate 7 there is a means (not shown) for arranging a mixer nozzle 10, indicated by dot-and-dash lines. This has, at its end facing the holding plate 7, two inlet openings which communicate in a known manner directly or indirectly with the outlet openings of the cartridges 5. The feature, namely that the cartridges are arranged alongside each other, is intended only to signify that they are arranged such that they can be operated simultaneously and synchronously. A positional restriction going beyond this, for example restriction to a parallel arrangement, in not thereby intended, although this is obviously advantageous.

The cartridges 5 contain plungers. These can optionally be omitted if the cartridges contain foil bags. The stamps then take the place of the plungers mentioned in the claim. For advancing the plungers or the rear face of the bags, the apparatus has stamps 11 which, in the drawing, are shown in the state in which they are retracted into the rear holding plate 6 for the purpose of changing the cartridges. They are arranged at the front end of stamp rods 12, whose rear ends are secured rigidly in a cross bracket 13 which, by means of a threaded spindle 14, can be advanced in the direction of the mixer nozzle or retracted in the opposite direction. The stamps 11 can optionally be changed if cartridges of different diameter are to be used. Their distance from one another can also be variable. When the cartridges 5 are fitted in the apparatus, the stamps 11 are advanced by advancing the cross bracket 13 until they reach the plungers in the cartridges 5. This advance movement can be triggered automatically by the insertion of the cartridges or can be triggered manually by switching on the apparatus.

For the advance and return of the threaded spindle 14, a motor 15 with gear 16 is provided, the drive movement of which is transmitted to the threaded spindle 14 via a belt transmission 17. For mounting the threaded spindle 14 and the annular discs belonging to the belt transmission 17, means (not shown) are provided which are disposed on the plate 3 and on a further frame plate 20 which is connected rigidly to the plate 3 via columns 21.

A further motor 22 is arranged on the plate 20 and is connected (in a manner not shown) on the drive side to a mixer drive shaft 23 which lies between the plates 3 and 20 coaxially within the threaded spindle 14, is guided between the cartridges 5 from the rear holding plate 6 to the front holding plate 7, and is mounted in the latter. It protrudes from the front holding plate 7 in the form of a projection 24 which, for the purpose of rotational connection to the mixer shaft (not shown), is of polygonal design (not shown) for example. The shaft projection 24 can be pushed back counter to a spring force until it no longer protrudes from the front holding plate 7. It can also be arranged in such a way that when the stamps 11 are completely retracted for the purpose of cartridge exchange, it is likewise retracted into the front holding plate 7 in order to make it easier to attach a new mixer nozzle 10.

An electronic unit 30 is provided and is indicated diagrammatically at 30. The first function of this electronic unit is to constantly regulate the speed of rotation of the motor at a predetermined value when the motor is in pressing-out mode and loaded. This is the function which guarantees the constant mixing result.

A second function of the electronic unit 30 is to measure the current consumption of the motor 15 in order to ascertain whether the latter is loaded or unloaded. In the former case, it is to be assumed that the stamps 11 are bearing on the cylinders of the cartridges 5 and the pressing-out resistance of the cartridges is causing the high current consumption measured by the unit 30. In this case, the electronic unit 30 ensures that the motor 15 is operated at the predetermined advance speed.

If, by contrast, the electronic unit ascertains that the current consumption lies below a value which is normally achieved only when the drive is loaded, it ensures that the motor 15 is operated at a higher speed (for example ten times faster). This applies independently of the direction of rotation of the motor 15.

In the third place, the electronic unit 30 ensures that the motor 22 is operated at a high mixing speed if the drive 15 is loaded. Conversely, it ensures that the motor 22 is operated at a substantially lower speed (for example at a tenth or a twentieth of the mixing speed) if the motor 15 is not loaded in the advance mode. In reverse mode, the drive of the mixer is automatically stopped.

A sensor (not shown) is arranged in such a way that it responds when the advance stamps 11 reach their furthest advanced position, which corresponds to complete emptying of the cartridges 5. If the sensor responds in this position, it causes the electronic unit 30 to reverse the direction of rotation of the motor 15 so that the stamps 11 are drawn back from the cartridges, and in a rapid movement, because they are not loaded at that time. A second sensor (not shown) ascertains when the stamps 11 have reached their completely retracted position shown in the figure. It then causes the motor 15 to stop. The withdrawal of the stamps 11 can also be triggered manually with the aid of a switch (not shown) if cartridges are to be changed before they are empty.

When the stamps 11 are retracted, the cartridges 5 can be changed. The motor 15 is started up again automatically after the insertion of the new cartridges or by manual means. Since the stamps 11 are at first not loaded, they advance in a rapid movement until they reach the plungers of the cartridges 5. The current consumption then increases and the electronic unit 30 switches the motor 15 to its low rotational speed, which is to be kept constant.

When the stamps 11 are retracted, the projection 24 of the mixer drive shaft 23 is also preferably retracted so that the mixer nozzle 10 can be easily changed. When the advance movement of the stamps 11 commences after the cartridges have been changed, the motor 22 is also started up again, initially at a low speed as long as the electronic unit 30 does not detect any load state. The shaft projection 24 of the mixer drive shaft 23 then has sufficient time to find the appropriate engagement position in relation to the coupling part of the mixer shaft and, as a result of the spring pressure loading it, to mesh into the coupling position. Only when the stamps 11 have reached the plungers of the cartridges 5 and the electronic unit 30 accordingly detects the load state is the motor 22 accelerated to the high speed of rotation which corresponds to the mixer mode. At the end of an application, the advance is stopped by pressing a button, and in this way a slight return movement of the motor 15 is triggered at the same time, which relieves the load on the system.

Figure 2:
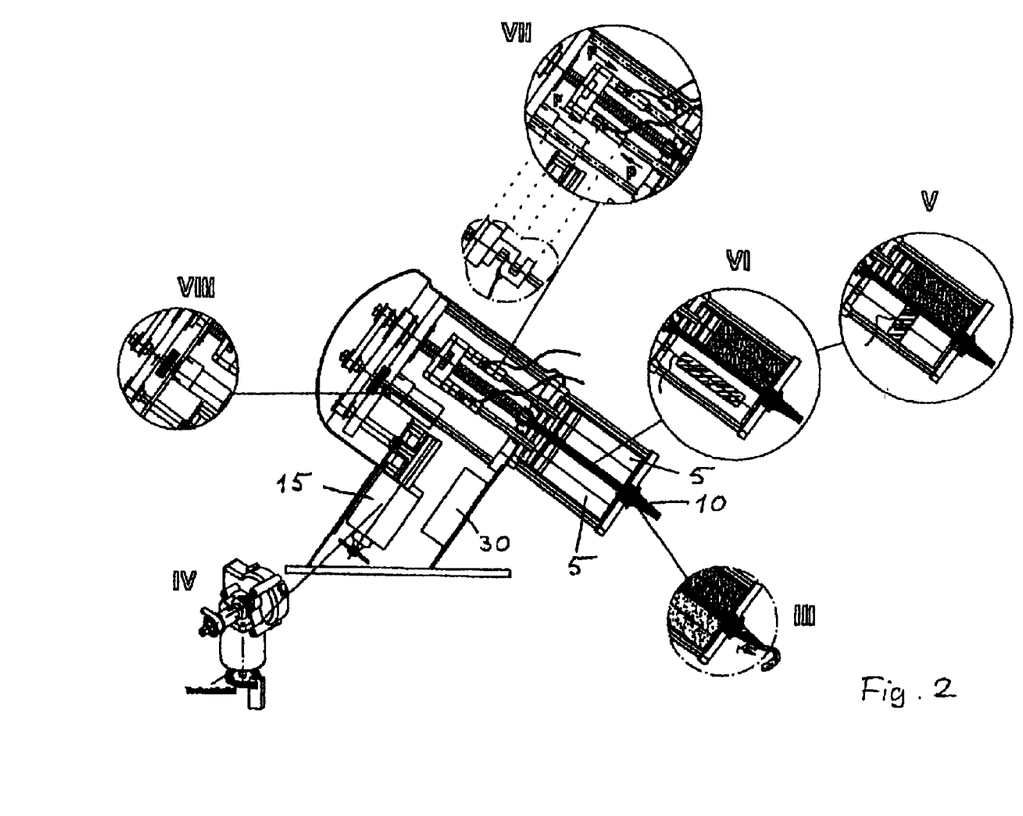
FIG. 2 shows an apparatus of the type shown in FIG. 1, in which measurement means according to the invention are provided, shown in more detail at III to VIII.

FIG. 2 shows an apparatus which is fitted according to the invention with sensors. A relatively large number of sensors is shown here, but this does not mean that all sensors must always be present. Simply for the sake of clarity, these sensors are shown in a single drawing. The details of the sensor arrangements indicated at III to VIII are shown on a larger scale in FIGS. 3 to 8. A crucial feature, however, is the central electronic unit 30 in which data concerning the pressing-out behaviour of known components are stored and which compares these stored data with measured data, and if appropriate also carries out calculations to take account of various parameters and then regulates the speed of the advance motor and/or of the mixer motor in a favourable manner.

Figure 3:
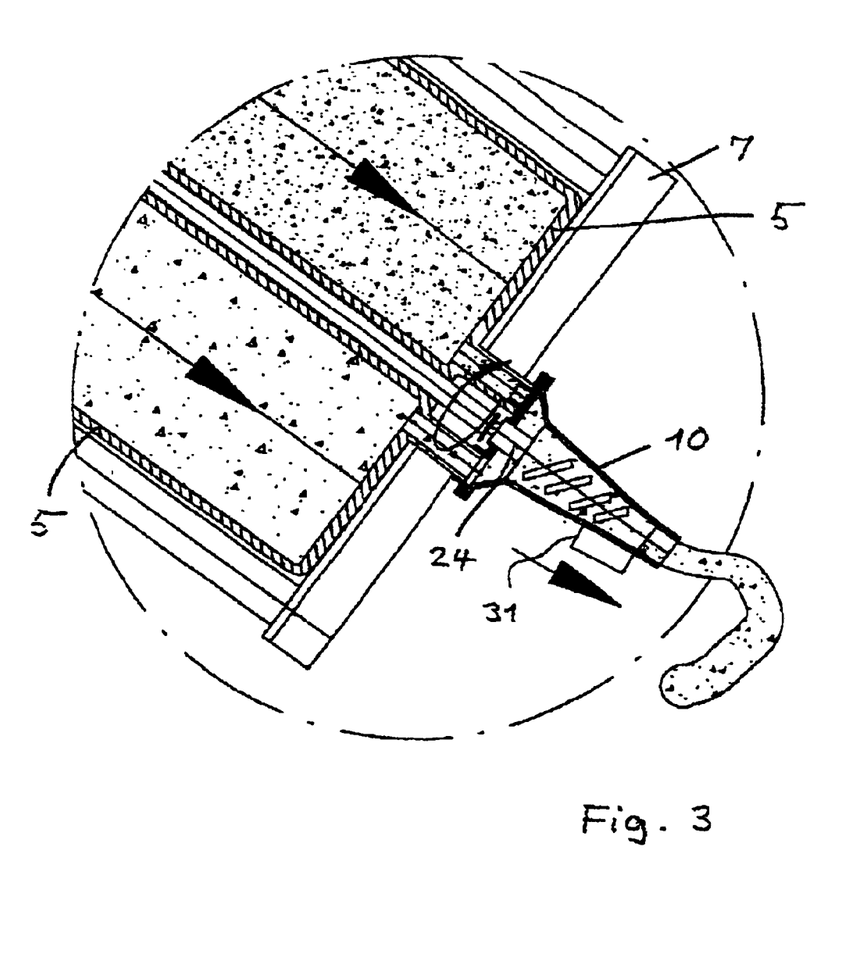
FIGS. 3 to 8 show the partial representations III to VIII from FIG. 2 on an enlarged scale.

FIG. 3 shows a thermocouple 31 which is applied on the outer wall of the mixer nozzle 10 and measures the temperature of the multi-component compound.

Figure 4:
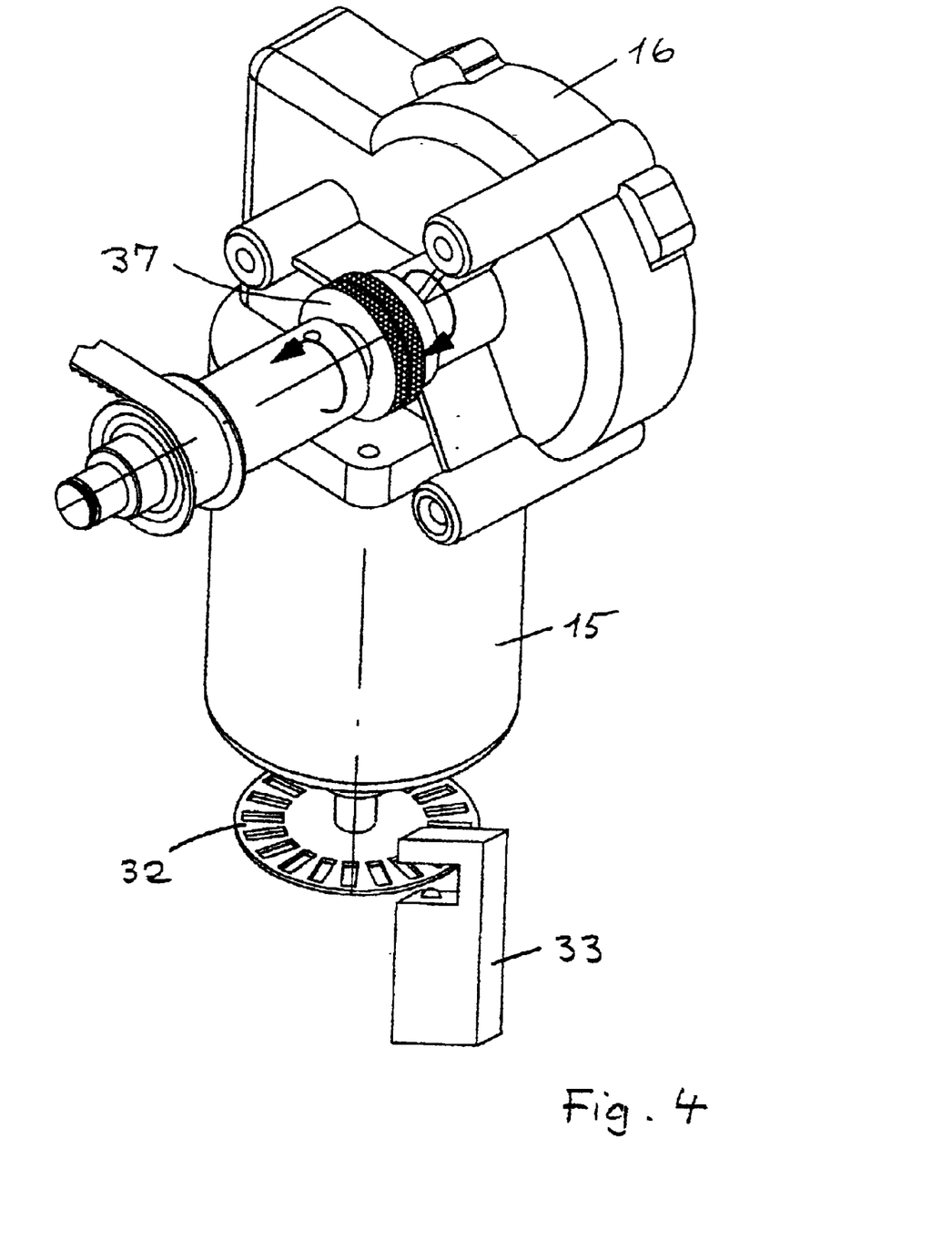

FIG. 4 shows a tachometer disc 32 with slits and a light barrier 33 with which the speed of rotation of the advance motor 15 is measured. Also shown is a torque measurement cell 37 for measuring the drive moment applied by the advance motor 15.

Figure 5:
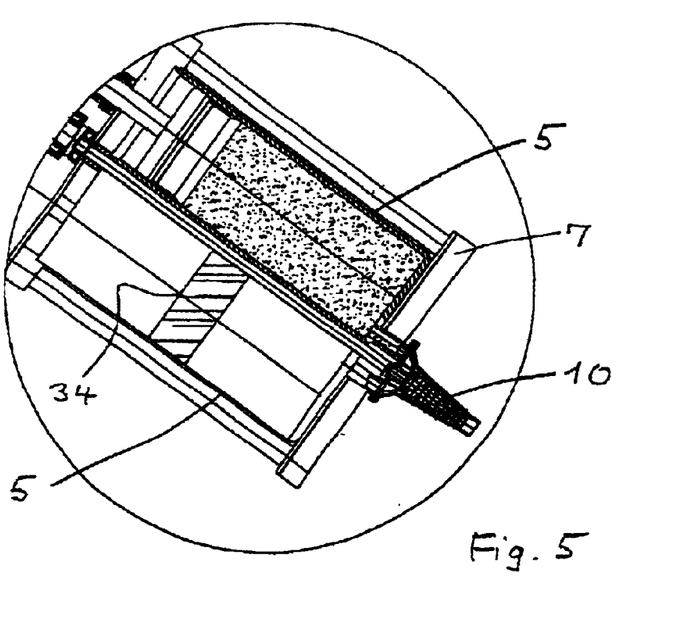

FIG. 5 shows a strain gauge 34 which extends radially about the cartridge 5 in order to measure the deformation of the cartridge in the circumferential direction.

Figure 6:
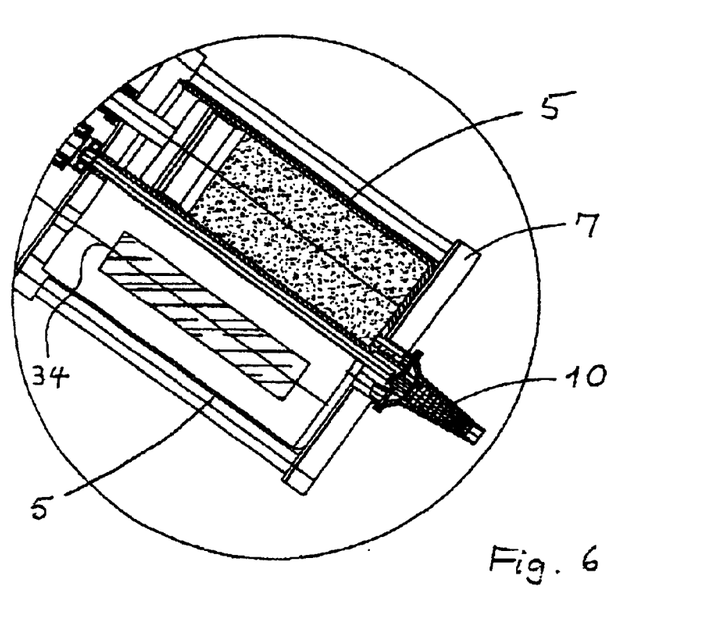

In FIG. 6, the strain gauge 34 is applied in the axial direction in order to measure the expansion in this direction.

Figure 7:
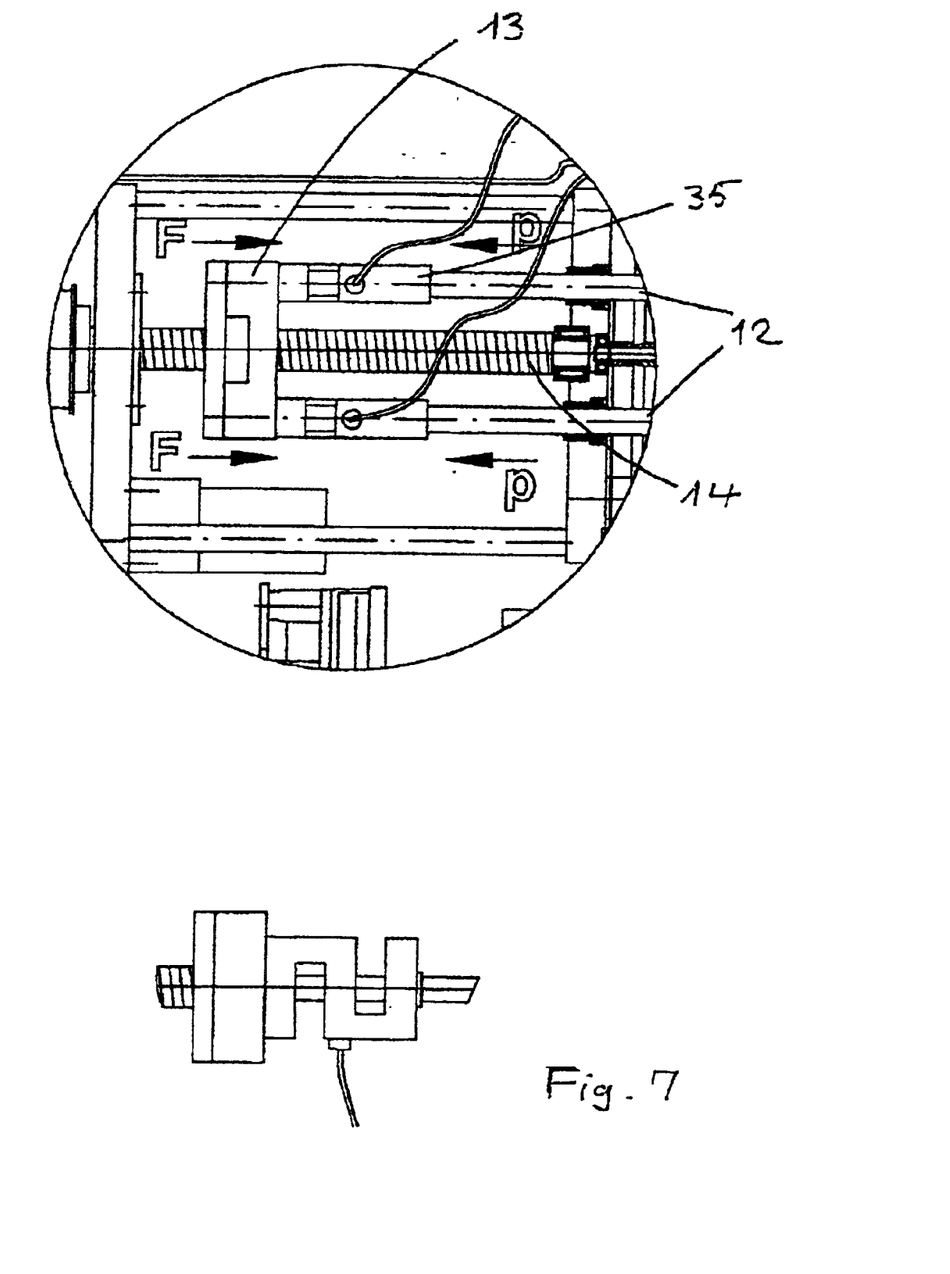

FIG. 7 shows pressure measurement cells 35 which measure the pressure with which the stamps 11 are acted upon via the stamp rods 12. In the lower part of FIG. 7, a view is shown from the side parallel to the plane of the drawing of the upper part of FIG. 7.

Figure 8:
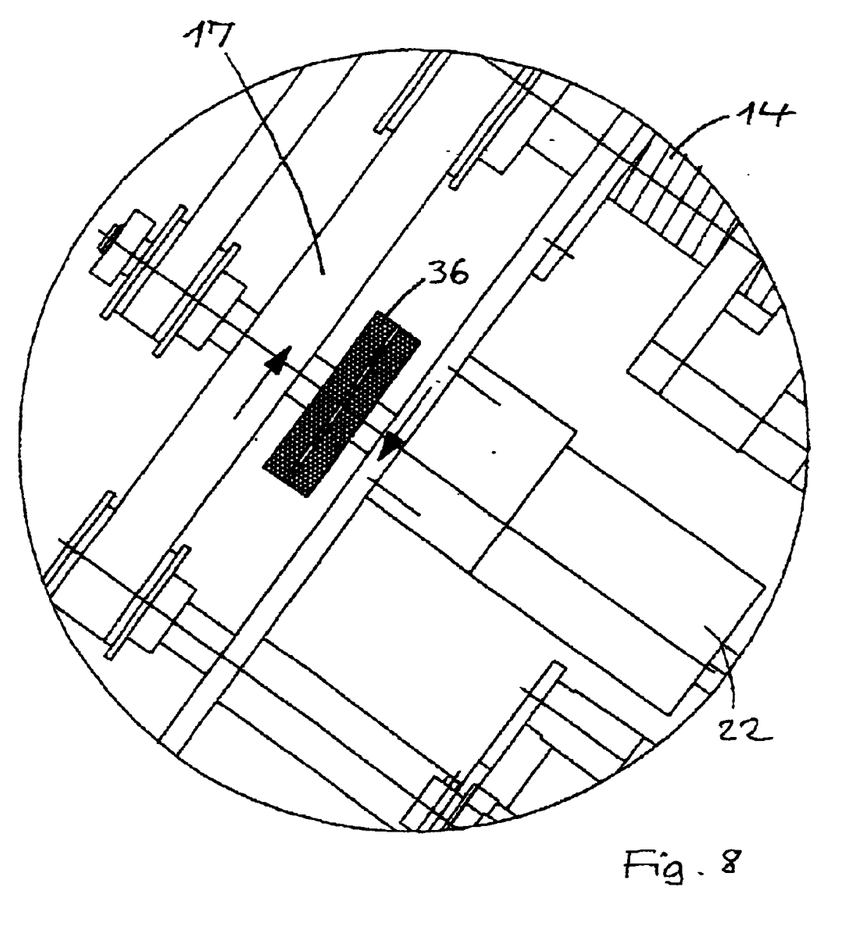

Finally, FIG. 8 shows a measurement cell 36 with which the torque of the mixer drive shaft 23 is measured.

The measurement sensors in FIGS. 3 to 8, insofar as they are provided, are connected in a manner not shown to the central electronic unit 30 in order to deliver signals concerning the pressing-out behaviour to the unit 30, which then regulates the drive speeds of the motors 15 and 22.

What is claimed is:

1. A method for generating a multi-component compound by pressing components of the compound out of exchangeable cartridges each having a plunger and an opening, wherein said cartridges are arranged alongside one another and open into a mixer, said pressing is accomplished by jointly advancing in a regulated manner the plungers by means of an electric drive, and an advance speed of the plungers is regulated, characterized by comparing a measured property measured during the pressing-out of the components with either stored or calculated values for known materials and adjusting the advancement of the plungers to a desirable rate based on the comparison.

2. The method according to claim 1, characterized in that the measured property measured during the pressing-out of the components is a current consumption or a torque of the electric drive.

3. The method according to claim 1, characterized in that the measured property measured during the pressing-out of the components is a pressure of at least one of the components.

4. The method according to claim 2, characterized in that the measured property measured during the pressing-out of the components is the advance speed of the plungers.

5. The method according to claim 1, characterized in that the measured property measured during the pressing-out of the components is a deformation of at least one of the cartridges.

6. The method according to claim 1, characterized in that the measured property measured during the pressing-out of the components is a deformation of a cartridge holder.

7. The method according to claim 1, characterized in that the components are mixed using a mixer driven by an electric motor, and a current consumption or a torque of the mixer electric motor is measured.

8. The method according to claim 7, characterized in that the speed of rotation of the electric motor for the mixer is regulated.

9. A method for generating a multi-component compound by pressing components of the compound out of exchangeable cartridges each having a plunger and an opening, in which said cartridges are arranged alongside one another and open into a mixer, said mixer is driven by an electric motor wherein the speed of rotation of the electric motor is regulated and a current consumption or a torque of this electric mixer motor is measured, and said pressing is accomolished by jointly advancing in a regulated manner the plungers by means of an electric drive, wherein an advance speed of the plungers is regulated by comparing a measured property measured during the pressing-out of the components with either stored or calculated values for known materials and adjusting the advancement of the plungers to a desirable rate based on the comparison and further characterized in that a temperature of at least one of the components is measured.

10. The method according to claim 9, characterized in that the temperature of the components is measured in the mixer.

11. A device for generating a multi-component compound by pressing out and mixing the multi-component components from a set of cartridges which open into a mixer and which are arranged in an exchangeable manner in the device, wherein said device includes an electric motor for the joint regulated advancement of the set of plungers, and each plunger of the set of plungers is associated with a cartridge of the set of cartridges, characterized in that the device has a means for measuring as pressing-out behavior of the components, a storage means for storing the pressing-out behavior of known materials, and a comparing and calculating means for comparing the stored and measured pressing-out behavior with a measured value which is generated by the means for measuring, and a regulating means for regulating the advancement of the set of plungers based on a comparison between the stored and measured pressing-out behavior and the measured value.

12. The device according to claim 11, characterized in that the means for measuring measures a current consumption or a torque of the electric drive for the advancement of the set of plungers.

13. The device according to claim 11, characterized in that the means for measuring measures a pressing-out pressure of at least one of the components.

14. The device according to claim 11, characterized in that the means for measuring measures an advancement rate of the set of plungers.

15. The device according to claim 11, characterized in that the means for measuring measures a deformation of at least one of the cartridges.

16. The device according to claim 11, characterized in that the means for measuring measures a deformation of the cartridge holder.

17. The device according to claim 11, characterized in that it has a mixer, driven by an electric motor, and means for measuring a current consumption or a torque of the electric motor.

18. The device according to claim 17, further comprising a means for regulating the speed of rotation of the electric motor for the mixer.

19. Device according to claim 12, characterized in that it has a mixer, driven by an electric motor, and means for measuring the electric consumption or the torque of the electric motor.

20. Device according to claim 13, characterized in that it has a mixer, driven by an electric motor, and means for measuring the current consumption or the torque of the electric motor.

21. A device for generating a multi-component compound by pressing out and mixing the multi-component components from a set of cartridges which open into a mixer and which are arranged in an exchangeable manner in the device, wherein said device includes an electric motor for the joint regulated advancement of a set of plungers and each plunger of the set of plungers is associated with a cartridge of the set of cartridges, a means for measuring a pressing-out behavior of the components, a storage means for storing the pressing-out behavior of known materials, and a comparing and calculating means for comparing the stored and measured pressing-out behavior with a measured value which is generated by the means for measuring, and a regulating means for regulating the advancement of the set of plungers based on a comparison between the stored and measured pressing-out behavior and the measured value, and, further comprising a temperature measurement component.

* * * * *

UNITED STATES PATENT AND TRADEMARK OFFICE
CERTIFICATE OF CORRECTION

PATENT NO.        : 6,932,237 B2
APPLICATION NO.   : 10/200356
DATED             : August 23, 2005
INVENTOR(S)       : Heymann et al.

It is certified that error appears in the above-identified patent and that said Letters Patent is hereby corrected as shown below:

Column 6:

Line 57, delete "accomolished" and substitute --accomplished--.

Column 7:

Line 9, after "measuring" delete "as" and substitute --a--.

Column 8:

Line 8, delete "Device" and substitute --The device--.

Line 9, after "mixer" delete ",".

Line 10, delete "the electric" and substitute --a current-- and before "torque" delete "the" and substitute --a--.

Line 12, delete "Device" and substitute --The device--.

Line 13, after "mixer" delete ",".

Line 14, before "current" delete "the" and substitute --a-- and before "torque" delete "the" and substitute --a--.

Signed and Sealed this

Fifteenth Day of August, 2006

JON W. DUDAS
*Director of the United States Patent and Trademark Office*